United States Patent
Aue et al.

(10) Patent No.: US 7,258,691 B2
(45) Date of Patent: Aug. 21, 2007

(54) WORKING INSTRUMENT WITH HANDLE ELEMENT FOR USE IN A RESECTOSCOPE, AND HANDLE ELEMENT FOR A WORKING INSTRUMENT

(75) Inventors: Thomas Aue, Hamburg (DE); Felix Nussbaum, Hamburg (DE); Thomas Wosnitza, Lüneburg (DE)

(73) Assignee: Olympus Winter & IBE GmbH, Hamburg (DE)

( * ) Notice: Subject to any disclaimer, the term of this patent is extended or adjusted under 35 U.S.C. 154(b) by 496 days.

(21) Appl. No.: 10/947,842

(22) Filed: Sep. 23, 2004

(65) Prior Publication Data

US 2005/0070893 A1    Mar. 31, 2005

(30) Foreign Application Priority Data

Sep. 26, 2003 (DE) ................. 103 45 111

(51) Int. Cl.
 *A61B 18/18* (2006.01)
(52) U.S. Cl. ............................. 606/46; 606/1
(58) Field of Classification Search ............... 606/1, 606/41, 45–50
See application file for complete search history.

(56) References Cited

U.S. PATENT DOCUMENTS

| 4,134,406 | A | * | 1/1979 | Iglesias ...................... 606/46 |
| 4,744,361 | A | | 5/1988 | Karasawa |
| 5,169,397 | A | | 12/1992 | Sakashita et al. |
| 5,591,181 | A | | 1/1997 | Stone et al. |
| 6,893,441 | B2 | * | 5/2005 | Brommersma et al. ....... 606/46 |
| 2002/0193792 | A1 | | 12/2002 | Valencic et al. |
| 2003/0130693 | A1 | | 7/2003 | Levin et al. |

FOREIGN PATENT DOCUMENTS

| DE | 100 42 097 C1 | 12/2001 |
| DE | 101 22 465 C1 | 8/2002 |

\* cited by examiner

*Primary Examiner*—Michael Peffley
(74) *Attorney, Agent, or Firm*—Rankin, Hill, Porter & Clark LLP

(57) ABSTRACT

A working instrument for use in a resectoscope with a pushing force-transmitting elongated support, whose proximal end area includes an attachment section for attachment in a resectoscope, and whose distal end area carries a working device. The working instrument includes, in its distal end area, a handle element. The handle element projects in a distal direction beyond the support and the working device and is connected to the working instrument so as to transmit pushing forces and can be removed.

10 Claims, 3 Drawing Sheets

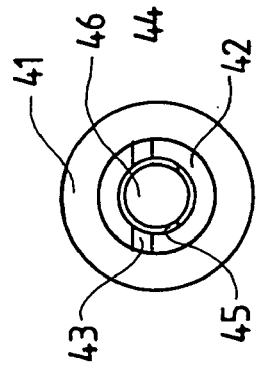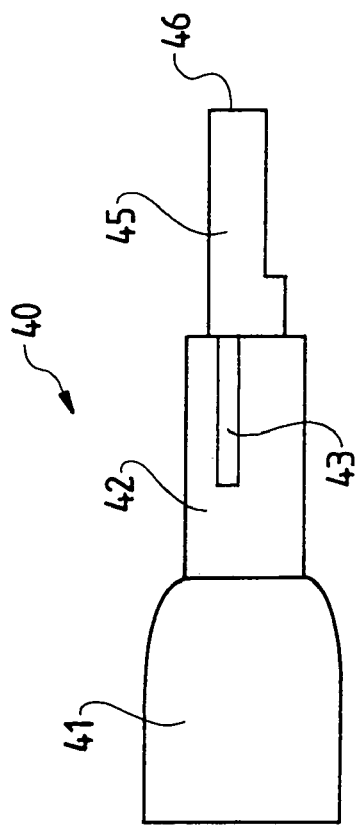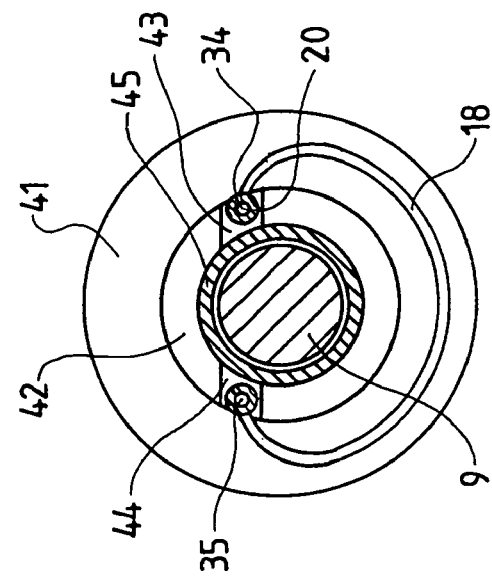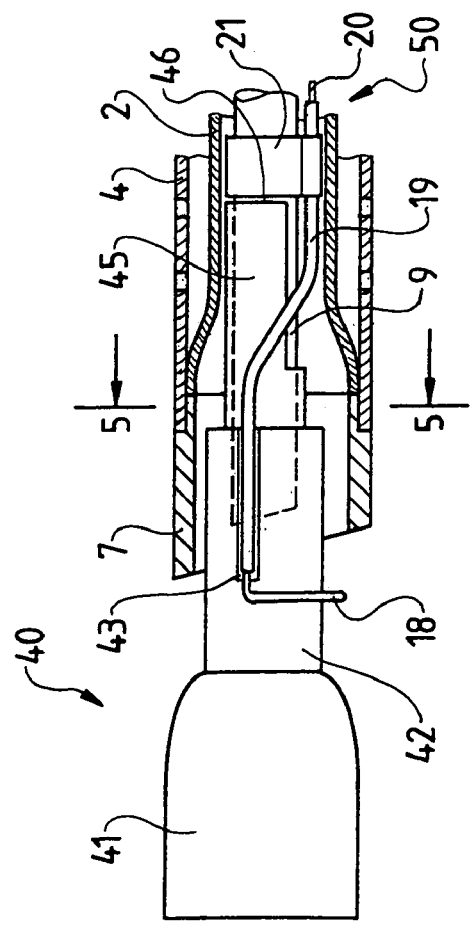

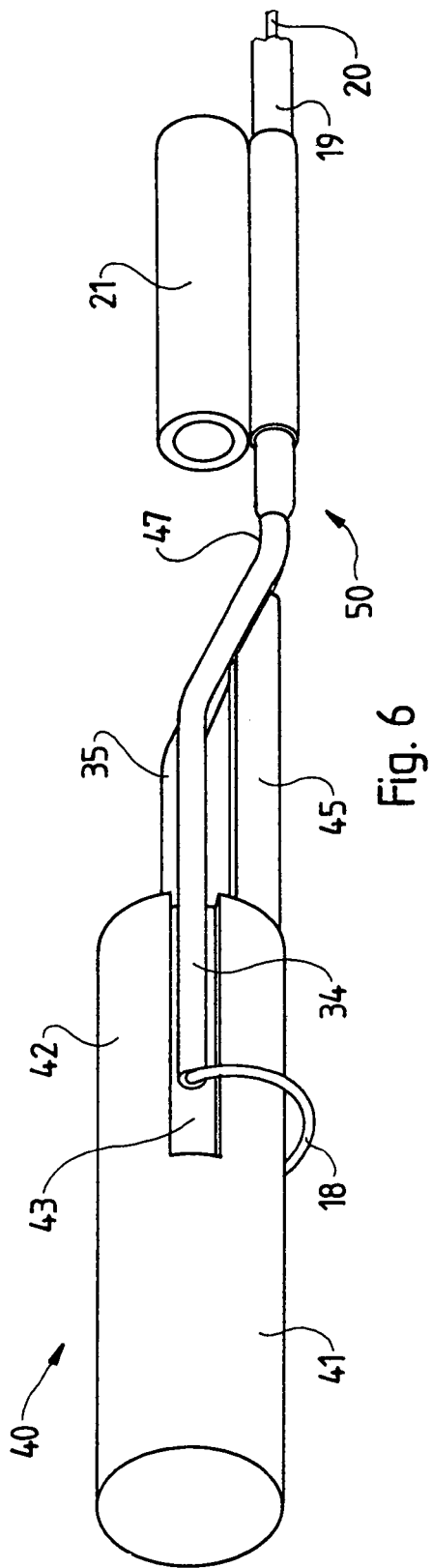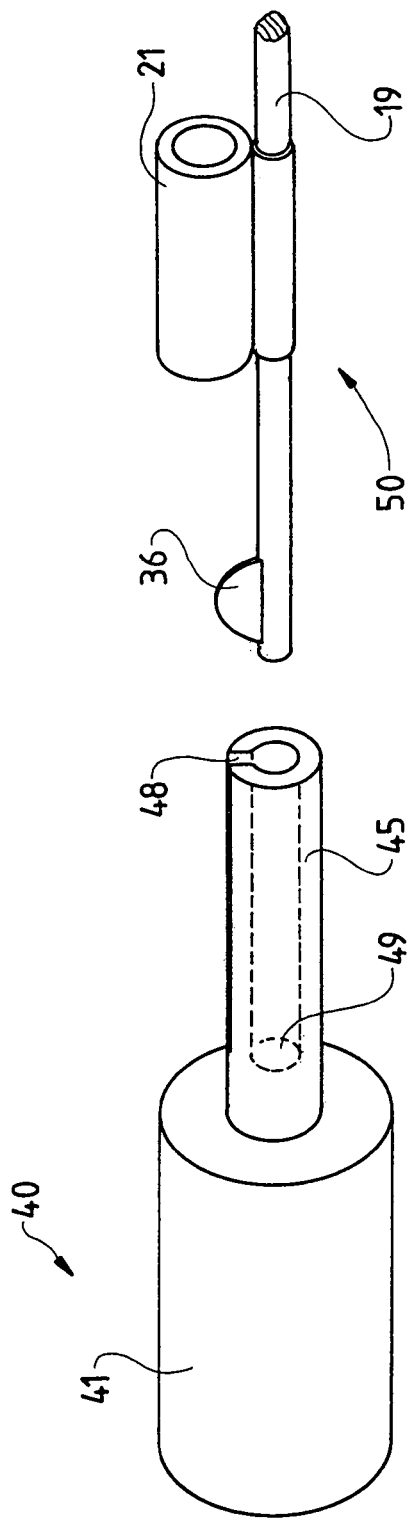

WORKING INSTRUMENT WITH HANDLE ELEMENT FOR USE IN A RESECTOSCOPE, AND HANDLE ELEMENT FOR A WORKING INSTRUMENT

BACKGROUND OF THE INVENTION

Working instruments of the type of the present invention are used in conjunction with resectoscopes, e.g. in urology or gynaecology. For this purpose, the working instruments are inserted into the resectoscope and then advanced through orifices and channels of the body, e.g. the urethra, to the desired treatment site, e.g. the prostate.

Working instruments of this type consist of a long actuator rod, which can be attached in the sliding body of a resectoscope with their proximal end. On its distal end, the working instrument comprises a working device, e.g. a cutting loop to which a HF current can be applied, a cold knife, a curette or other devices known from the state-of-the-art, which allow the surgeon to perform the desired treatment, e.g. resection of the prostate, at the treatment site.

Modern resectoscopes are provided as continuous irrigation resectoscopes, in which the continuous irrigation of the operative field provides a clear view of the operative field to the surgeon. For this purpose, the resectoscopes comprise two separate channels, one of which is provided for the supply of irrigation fluid and the other is provided for the return of the contaminated fluid. A proven design providing these two channels are double-sheath endoscopes, such as shown e.g. in DE 100 42 097.4. In the following, the invention is illustrated in more detail as an example of a double-sheath endoscope without limiting the scope of the invention to this particular design of endoscope.

The resectoscope shown in DE 100 42 097.4 consists of an external and an internal sheath, a main body, a working instrument with cutting loop and guiding sleeve, a guiding tube with end-piece, a sliding body, and a telescope with eye-piece. For assembly, the telescope is inserted from a proximal end into the guiding tube, which is firmly connected to the main body and on which the sliding body is borne such that it can be displaced in an axial direction. Then, the working instrument with its attachment area leading is advanced from a distal end through a bore in the main body to the sliding body, and attached in the sliding body. During the advancement of the working instrument, the guiding sleeve slides over the telescope. Finally, the internal sheath, which is provided in the shape of an elongated tube, is pushed over the telescope and the working instrument, and coupled to the main body.

The external sheath, which is also provided in the shape of an elongated tube and may have a filling rod inserted into it, is introduced into the body of the patient by the surgeon. After removal of the filling rod, the resectoscope, assembled as described above, is then introduced through the hollow external sheath and the external sheath is also coupled to the resectoscope. At this point, the surgeon can commence the operation.

One problem associated with the type of assembly illustrated above is that the working instrument must be held with the fingers while it is being inserted through the bore in the main body and until it is locked in the sliding body. The working instrument is held either at the actuator rod, the guiding sleeve or at its distal end. However, neither of these areas possesses particularly good handling features, especially the distal end area of the working instrument which usually is not particularly resistant to the impact of forces applied to it. Consequently, there is a risk of damaging the working instrument. Moreover, there is a risk of injury if the working instrument bears a sharp-edged working device.

DE 101 22 465.6 shows a double-shaft resectoscope with a cutting loop as the working device, whereby the cutting loop has a larger diameter than the internal sheath. This means that the working instrument can no longer be guided through the internal sheath without damaging the cutting loop. For this reason, the assembly of this resectoscope must deviate from the procedure detailed above in that the internal sheath is pushed over the telescope and connected to the main body first. Only thereafter it is possible to insert the working instrument with its attachment area leading from a distal end through the internal sheath.

The internal sheath of the design shown in DE 101 22 465.6 is only slightly shorter than the working instrument. Therefore, almost the entire working instrument is inside the internal sheath during its insertion such that it can be grasped only at its distal end area, on which the cutting loop is arranged also. The handling problems described above are even more pronounced in this design.

It is therefore an object of the present invention to provide a working instrument, which simplifies the insertion into a resectoscope and remedies the described problems through the use of simple means.

BRIEF SUMMARY OF THE INVENTION

According to the invention, the working instrument comprises in its distal end area a handle element which projects in a distal direction beyond the support and the working device, which is resistant to pushing forces and connected to the working instrument, e.g. by the support, the working device and/or a possibly provided guiding tube, such that it can be removed. The working instrument can be held at this handle element. Since the handle element projects in a distal direction beyond the support and the working device, it is ensured that an area for grasping the working instrument safely and without any hazard always remains outside of the sheath during the assembly. The only requirement is that the handle element has sufficient dimensions. After the attachment of the working instrument, the handle element can be removed and the working instrument employed for its intended use.

The handle element is connected to the working instrument by means of a positive locking engagement maintaining the axial alignment between handle element and support. This provides for the advantage of the handle element and the working instrument not being capable of swiveling relative to each other, i.e. their axial alignment being fixed. This eases the aimed insertion of the working instrument.

During insertion, the attachment area of the working instrument must be inserted into a relatively small bore in the main body, and the guiding sleeve must be guided over the telescope, whereby the guiding sleeve surrounds the telescope with little clearance in a positive interlocking fashion. Both steps, thus, require precision in the handling of the working instrument and often insertion is successful only after multiple back-and-forth rotation of the working instrument. To overcome this problem, the handle element is connected to the working instrument by means of a rotation-transmitting positive interlocking engagement. In this arrangement, rotation of the handle element causes the entire working instrument to rotate.

For insertion of the working instrument, it is usually necessary to push the working instrument back and forth axially repeatedly before one succeeds to maneuver the attachment area into the bore or the guiding sleeve over the telescope as described above. To overcome this problem, the handle element is connected to the working instrument by means of an axial non-positive clamping engagement. In this arrangement, moving the handle element axially also moves the working instrument axially.

The invention provides for multiple attachment configurations of the handle element to the working instrument and the possibility to remove the handle element from the instrument. This is an advantage when there is a need to switch between different working devices during an operation, e.g. between a cutting and a coagulation instrument. When a switch is desired, the working instrument in use can be removed by attaching its respective handle element and a different working device can be inserted. At a later time, the first working device can be reinserted and its handle element can be removed allowing the surgeon to resume the use of the first working instrument.

The working instruments illustrated herein are usually used for a single operation only. The invention provides for the use of the handle instrument with multiple fitting working instruments such that the handle element does not need to be disposed of with the corresponding working instrument after its proper use, but can be reused.

However, for multiple use of the handle element it is preferred for the handle element to be provided such that it can be sterilized, in particular by autoclaving. Suitable materials for the handle element are known from the state-of-the-art.

Moreover, it is preferred for a handle part, regardless of whether it is reusable or for single use, either to be stored sterile-packaged jointly in one package with a corresponding working instrument or to be sterile-packaged until use in its own separate package.

As an alternative, the handle element is firmly connected to the working instrument and the connection is provided such that it separates upon the application of a defined force. This ensures that the handle element and the working instrument remain joined and are prevented from inadvertent separation. For example, it is possible for the handle element to be glued on. The handle element and the working instrument can also be provided in the form of a single part. For separation, a predetermined breaking point can be provided in the form of a weakness of the material allowing the handle element to be removed, e.g. by pulling, rotating or bending or movements combining these elements.

The handle element, once it is separated from the working instrument, cannot be reconnected. This counteracts the risk of a working instrument designed for single use or a handle element designed for single use being used multiple times despite not being designed for multiple use.

Pushing forces applied to the handle element must be transmitted to the remainder of the working instrument. This could be facilitated, for example, by pushing the handle element on the support or working instrument up to an axial stop, although the handle element could also be connected by means of non-positive engagement to the support or working device. As a matter of principle, the transmission of force can be facilitated by any means. However, in a working instrument whose support comprises a guiding sleeve for guiding the electrode on a telescope of the resectoscope, it is advantageous for the handle element to be designed such as to transmit pushing forces to the guiding sleeve. The guiding sleeve is sufficiently stable to safely take up the applied forces.

In a working instrument with a cutting loop, to which HF current can be applied, and with a support, whose distal end area forks into two loop support arms, it is preferable for the handle element to be provided such as to transmit pushing forces to the forking site. As before, the forking site is provided to be sufficiently stable for the transmission of force.

It is advantageous for the handle element to be made of a plastic material. Plastic materials are inexpensive materials, and especially they are single-use materials, which can be manufactured in any shape, and possess the stability required for the handle element. Plastic materials for sterilization, and especially autoclaving, are available, if needed.

Subsequently, the invention is illustrated in more detail by means of embodiments, which are shown in the figures in a schematic and exemplary fashion.

BRIEF DESCRIPTION OF THE SEVERAL VIEWS OF THE DRAWINGS

FIG. 2 shows a side view of a first embodiment of a handle element, FIG. 3 shows a frontal view of the handle element depicted in FIG. 2, FIG. 4 shows a partial sectional side view of the distal end area of the resectoscope depicted in FIG. 1 with the handle element depicted in FIG. 2 attached to the working instrument, FIG. 5 shows a sectional view along the line 5-5 in FIG. 4, in which the external and the internal sheath of the resectoscope are not shown, FIG. 6 shows a second embodiment of a working instrument with a handle element, and FIG. 7 shows a third embodiment of the distal end area of a working instrument with the corresponding handle element detached.

DETAILED DESCRIPTION OF THE INVENTION

Figure 1:
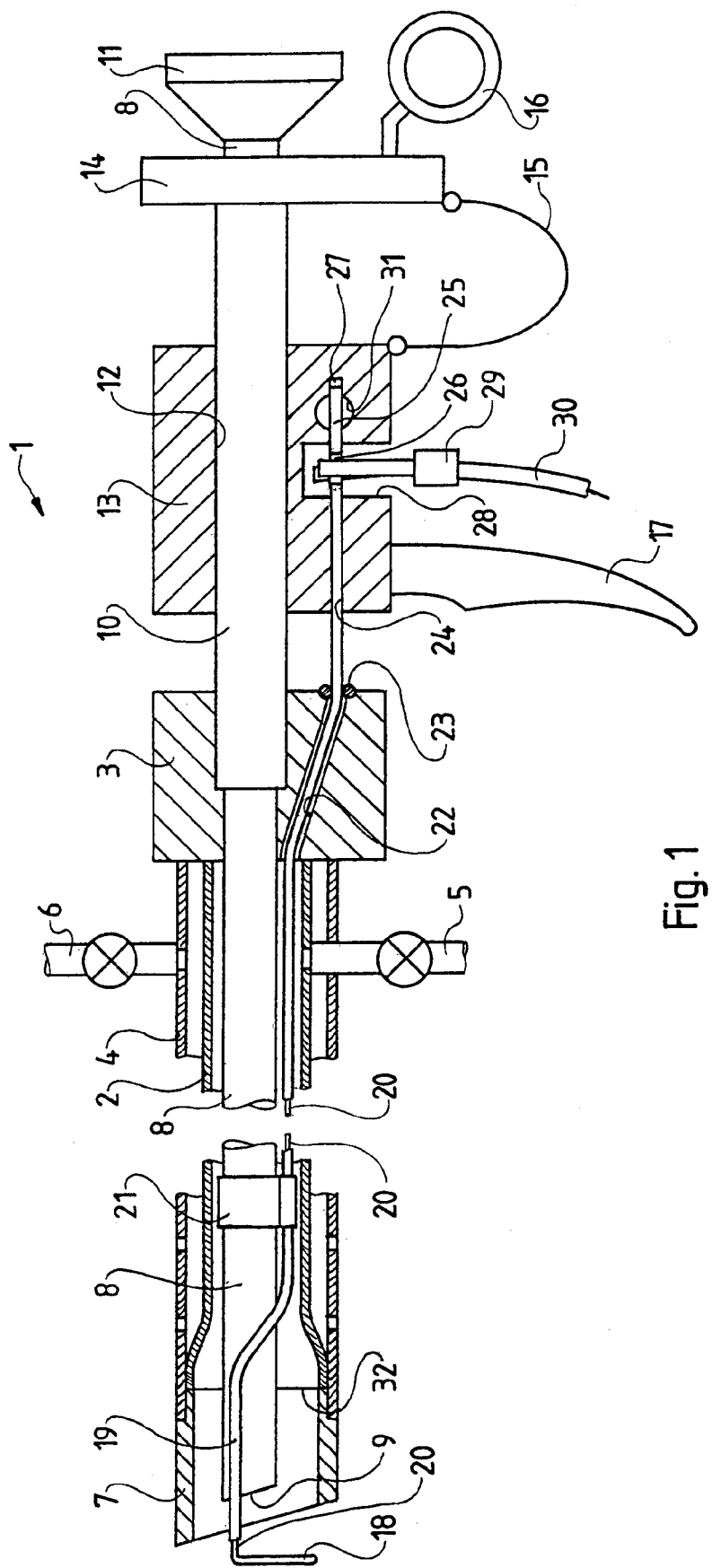
FIG. 1 shows a sectional side view of a double-sheath resectoscope with a working instrument installed.

FIG. 1 shows a sectional schematic view of a continuous irrigation resectoscope 1, as used for example for prostate resection, provided as a double-sheath endoscope. It comprises an internal sheath 2 whose proximal end is attached to a main body 3. In a fashion not shown, the internal sheath 2 can be attached to and removed from main body 3 by means of a common coupling device. Also attached to main body 3, an external sheath 4 surrounding internal sheath 2 is provided and can also have a common coupling which is not shown here. The inside of internal sheath 2 serves as a feed channel for continuous irrigation and can be accessed from outside, as shown in FIG. 2, via a connection 5 which is provided with valves and to which a hose can be connected. Another congeneric connection 6 for connecting another hose is connected to the annular gap between internal sheath 2 and external sheath 4, said gap serving as return channel.

The two sheaths 2, 4 are made of metal in a usual manner. The distal end section of the internal sheath 2 is provided to be insulating in a customary manner, for example in the form of ceramic end-piece 7. This insulating body 7 is attached to external sheath 4 in the example shown. The distal end area of internal sheath 2 is expanded and abuts on the proximal edge 32 of the insulating body 7.

Inside the internal sheath 2 and parallel to the axis extends a telescope 8, which, in the assembly position shown, views the working area in front of the ceramic end-piece 7 through its distal lens 9, and extends proximally through the main body 3. From there it extends further through a guiding tube 10, which is attached in main body 3, and ends beyond the proximal end thereof with an eyepiece 11, in place of which there can be a camera.

A sliding body 13 with a guiding bore 12 is borne on the guiding tube 10 such as to be displaceable in an axial direction. At the proximal end of guiding tube 10, an end-piece 14 is attached, opposite of which the sliding body 13 abuts elastically on a leaf spring 15 in the embodiment shown. A thumb ring 16 is arranged on end-piece 14, whereas a finger handle 17 is arranged on sliding piece 13. The surgeon can use one hand and place the thumb in thumb ring 16 and the index finger on finger handle 17 in order to move sliding body 13 in an axial direction. Alternatively, instead of the "active" actuation just described, a "passive" actuation can be provided, in which the leaf spring 15 is arranged between sliding body 13 and main body 3, and engagement sites 16, 17 also reside on these parts.

A replaceable electrode 18, to which HF current can be applied, is provided in the resectoscope shown, and a common design for prostate resection provides the electrode as a wire loop extending orthogonal to the direction of the axis. The electrode 18 is carried by an electrode support 19, which is provided in the form of an external insulation with an internal conducting wire 20. In a common design, the electrode support 19 is borne in a guiding sleeve 21 on the telescope 8 such as to be displaceable along the length of the telescope, and electrode support 19 extends through the sheath tube 2 to the main body 3. At main body 3, electrode support 19 extends through a laterally swiveled flow-through channel 22 with annular seal 23 for liquid sealing and extends from the proximal mouth thereof parallel to and at a larger distance from the axis to a receiving bore 24 in sliding body 13. The electrode 18, the electrode support 19, and the guiding sleeve 21 jointly form the working instrument 50.

In its proximal end area, the electrode support 19 comprises an attachment section 25 which forms its end-piece and is provided to be sufficiently stable, e.g. by being made of massive metal, for safe mechanical attachment of the electrode support in this place. Next to this on the distal side, the electrode support 19 comprises a engagement section 26, which is provided with an electrically conducting external surface, which is connected to the conducting wire 20 of the electrode support 19 in an electrically conducting fashion.

Moreover, the proximal end 27 of the receiving bore 24 forms a terminal stop for the electrode support 19, up to which the electrode support 19 can be inserted into receiving bore 24 in proximal direction.

When the electrode support 19 in the assembly position shown is inserted fully into the receiving bore 24 of the sliding body 13 up to the terminal stop 27, its engagement section 26 resides in a recess 28 of sliding body 13, in which the engagement section 26 is readily accessible from outside. In this place it can be contacted for example to the clamping plug 29 at the end of a cable 30, which connects to a HF generator not shown here.

Directly proximal to recess 28 and in the area of the attachment section 25 of the electrode support 19, an attachment device is provided in the sliding body 13. In the embodiment, this attachment device comprises a transverse bore 31, which can be provided e.g. with an internal thread for screwing-in a clamping screw. Alternatively, the attachment device may be provided in another fashion, e.g. with a slider engaging a groove, in the form of a snap-in locking device or similar device.

Provided the electrode support 19 is properly attached and contacted in the sliding body 13, the described pushed movement of the sliding body 13 can be used to displace the entire electrode support 19 with electrode 18 in a longitudinal direction relative to the sheath tube 2. While monitoring with the telescope 8, high frequency current can be applied to the electrode 18 and the electrode can be used for cutting while performing an axial motion.

In order to replace the electrode 18, the clamping plug 29 is removed and the attachment device (transverse bore 31) is loosened. Subsequently, the entire electrode support can be pulled out of the resectoscope 1 in a distal direction. Reversing this procedure, a new electrode can be inserted in a proximal direction up to the terminal stop 27, and then mechanically attached and contacted. The arrangement allows the electrode support 19 to be mechanically attached to the transverse bore 31 first and the proper function to be tested by sliding the sliding body 13 back and forth, before effecting the contacting with the clamping plug 29.

In the embodiment shown, the electrode support 19 supports an electrode 18, which is provided in the form of a common resection loop. However, electrodes with other shapes can be provided equally well, for example button electrodes, pin electrodes, roller electrodes or knife-shaped electrodes acting coagulating, vaporizing or cutting upon the application of HF current. However, it is also possible to use working instruments with working devices, to which no HF current can be applied, such as knives, curettes, etc.

Usually, the guiding tube 10 with end-piece 14, the sliding body 13, and the main body 3 are pre-assembled. Then, the telescope 8 is pushed from a proximal end with its lens 9 leading through guiding tube 10 and attached once it reaches its end position. Subsequently, the internal sheath 2 is pushed from a distal end over the telescope 8 and coupled to the main body 3. Only then the working instrument 50 is inserted by inserting it from a distal end into the internal sheath 2 with the attachment section 25 of the support 19 leading. In this step, the guiding sleeve 21 has to be guided over the telescope 8, and the attachment section 25 has to be advanced through the bore 22 in the main body 3, in order to access the receiving bore 24 in the sliding body 13. The electrode support 19 is pushed up to the terminal stop 27 and then snapped-in. And finally, the thus assembled resectoscope 1 can be inserted into the external sheath 4, which has previously been placed in the body of the patient, and the external sheath 4 can then also be coupled to the resectoscope 1.

FIGS. 1 and 2 show a handle element 40, which simplifies the insertion of a working instrument 50 according to the description above into a resectoscope 1. The handle element 40 consists of a handle area 41 used by the surgeon to hold the handle element 40. In order to improve the grasping features, the handle area 41 may comprise a corrugated or comparably structured surface.

Adjacent to the handle area 41, a middle area 42 is provided, which is cylindrical in shape and has a smaller diameter than the handle area 41. Two grooves 43, 44 extending in an axial direction in its external surface are provided. Adjacent to the middle area 42, a tip area 45 is provided, which is also cylindrical in shape and has an even smaller diameter than the middle area 42. The tip area 45 is provided in the shape of a tube, whereby a lower part of the tube is cut off such that a roof-like area remains.

FIGS. 4 and 5 show the handle element 40 and the working instrument 50 in conjunction. In addition, they show the arrangement of the handle element 40 and working instrument 50 in the resectoscope 1.

To push the handle element 40 onto the working instrument 50, the tip area 45, whose diameter is smaller than that of the cutting loop 18 of the working instrument 50, is pushed in between the two loop support arms 34, 35 and in the direction of guiding sleeve 21. Moreover, the tube diameter of the tip area 45 is selected such that the telescope 8 is surrounded by tip area 45 in a form-fitting fashion. The grooves 43 and 44 in the middle area 42 of the handle element 40 are provided such that they receive the two loop support arms 34, 35. The diameter of the middle area 42 is dimensioned such that the loop support arms 34, 35 are lightly pressed radially outward, whereby a clamping force is thus generated, which keeps the handle element 40 and the working instrument 50 connected in a non-positive fashion. The length of the tip area 45 is dimensioned such that its distal edge 46 abuts on the guiding sleeve 21. The tip area 45 and the grooves 43, 44 in the middle area 42 of the handle element 40 are dimensioned such that a sufficient length of the support arms 34, 35 is received in the grooves, 43, 44. And finally, the diameter of the middle area 42 is dimensioned such that the middle area 42 fits inside the internal sheath 2.

This provides for the connection between the handle element 40 and the working instrument 50 being such that rotational motions and axial back-and-forth motions of the kind required during the insertion of the working instrument 50 into the endoscope 1 in order to manoeuvre the attachment section 25 into the narrow bore 22 in the main body 3, and to align the guiding sleeve 12 relative to the telescope 8 to allow it to be pushed over the telescope 8, are made possible.

Whereas the working instrument 50 fully disappears inside the external sheath 40 when the sliding body 13 is pulled back, the handle area 41 of the handle element 40, when it is pushed onto the working instrument 50, remains fully outside of the resectoscope 1 and thus can be safely grasped. When the working instrument 50 is locked within resectoscope 1, the handle element 40 can be removed by pulling in an axial direction against the clamping forces of the support arms 34, 35 held in a clamping arrangement. The resectoscope 1 is now ready for use.

FIGS. 6 and 7 show alternative embodiments of a handle element 40. The handle element 40 of FIG. 6 differs from the handle element of FIGS. 2 to 4 not only in handle area 41 and middle area 42, which merge here without forming a step, but also by the tip area 45 comprising a lower elongated tube section, which tapers along its extension to the forking site 47 of the working instrument 50, which forms a terminal stop for the handle element 40. The pushing forces are transmitted to the forking site 47 in this second embodiment, whereas in the first embodiment illustrated above, the force was transmitted to the guiding sleeve 21. As before, the loop support arms 34, 35 are received in the axial groves 43, 44 in a non-positive fashion.

Following the insertion of the working instrument 50 into the resectoscope 1, the handle element 40 according to the second embodiment can be removed by simple pulling. However, the handle element 40 could also be firmly connected to the working instrument 50, e.g. by means of a glue connection between the tip area 45 and the forking site 47. In this case, the glue connection would have to be provided such that it is severed upon the application of a certain force, e.g. a pulling force. However, the separation should occur such that no fragments or sharp edges stay behind.

And finally, the handle element 40 of FIG. 7 shows a third embodiment. It is provided for a different working instrument 50, namely one with a cutting knife 36 as its working device. For this purpose, the tip area 45 of the handle element 40 is provided as a tube, the upper side of which comprises an axial slit 48, which receives the cutting knife 36 when the arrangement is pushed onto the working instrument 50. This form-fitting engagement between the handle element 40 and the working device 36 provides for the coupling of any rotation of the handle element 40 and working instrument 50. In addition, the internal diameter of the tube 45 can be selected such that the support 19 of the working instrument 50 is received in a clamping fashion. For this purpose, a narrow site can be provided for example. This provides for the handle element and the working instrument 50 to be connected to each other in a non-positive fashion in an axial direction also.

The handle element 40 of FIG. 7 can be pushed onto working instrument 50 up to an axial terminal stop. The terminal stop can be formed by the end of the slit 48, or the tip area 45 can be dimensioned such that the distal tip of the working instrument 50 abuts on an internal frontal surface 49. If the guiding tube 21 is to form a terminal stop, the end area 45 would have to be provided such that the telescope 8 is received without any interference.

The invention is not limited to the working devices shown. Rather, it also includes working devices, which fit through the internal sheath of a resectoscope. Moreover, the invention can also be applied to endoscopes other than the double-sheath endoscopes shown herein.

The invention claimed is:

1. A working instrument (50) for use in a resectoscope (1) in combination with a handle element (40), the working instrument including a pushing force-transmitting elongated support (19) having a proximal end area and a distal end area, said proximal end area comprising an attachment section (25) for attachment in a resectoscope (1), and said distal end area carrying a working device (18), wherein a handle element (40), which projects in a distal direction beyond the pushing force-transmitting elongated support (19) and the working device (18) and is connected to the working instrument (50) such that the handle element transmits pushing forces to the working instrument and can be removed, is provided in the distal end area of the working instrument (50).

2. The working instrument (50) and handle element (40) combination according to claim 1, wherein the handle element (40) is connected to the working instrument (50) via a form-fitting engagement providing for axial alignment between the handle element (40) and the support (19).

3. The working instrument (50) and handle element (40) combination according to claim 1, wherein the handle element (40) is connected to the working instrument (50) via a rotation-coupling form-fitting engagement.

4. The working instrument (50) and handle element (40) combination according to claim 1, wherein the handle element (40) is connected to the working instrument (50) via an axial force-transmitting clamping engagement.

5. The working instrument (50) and handle element (40) combination according to claim 1, wherein the handle element (40) is connected to the working instrument (50) such that the handle element can be connected and removed reversibly.

6. The working instrument (50) and handle element (40) combination according to claim 1, wherein the handle element (40) is firmly connected to the working instrument (50) and the connection is adapted to be severed upon application of a defined force.

7. The working instrument (50) and handle element (40) combination according to claim 1, wherein the handle element (40) is configured such that the handle element cannot be reconnected to the working instrument (50) once removed from the instrument.

8. The working instrument (50) and handle element (40) combination according to claim 1, wherein the support (19) comprises a guiding sleeve (21) for guiding the working instrument (50) on a telescope (8) of the resectoscope (1), and wherein the handle element (40) is adapted to transmit pushing forces to the guiding sleeve (21).

9. The working instrument (50) and handle element (40) combination according to claim 1, wherein the working device (18) is a cutting loop to which high-frequency current can be applied, and the support (19) forks into two loop support arms (34, 35) in its distal end area, and wherein the handle element (40) is adapted to transmit pushing forces to the forking site (47).

10. The working instrument (50) and handle element (40) combination according to claim 1, wherein the handle element (40) is made of plastic material.

\* \* \* \* \*